United States Patent [19]

Berger et al.

[11] Patent Number: 4,999,380

[45] Date of Patent: Mar. 12, 1991

[54] TREATMENT OF LIPOPROTEIN DISORDERS ASSOCIATED WITH CHOLESTEROL METABOLISM

[75] Inventors: Manfred Berger, Vienna, Austria; Daniele Spielmann, Lausanne; Helmut Traitler, Corseaux, both of Switzerland

[73] Assignee: Nestec S.A., Vevey, Switzerland

[21] Appl. No.: 259,156

[22] Filed: Oct. 18, 1988

[51] Int. Cl.$^5$ .............................................. A61K 31/70
[52] U.S. Cl. .................................. 514/558; 514/824; 424/195.1
[58] Field of Search ............................ 514/558, 824; 424/195.1

[56] References Cited

U.S. PATENT DOCUMENTS

| | | | |
|---|---|---|---|
| 3,993,775 | 11/1976 | Williams | 424/195.1 |
| 4,526,793 | 7/1985 | Ingenbleek et al. | 426/72 |
| 4,703,060 | 10/1987 | Traitler et al. | 514/549 |
| 4,776,984 | 10/1988 | Traitler et al. | 260/412.4 |

FOREIGN PATENT DOCUMENTS

| | | |
|---|---|---|
| 0271747 | 6/1988 | European Pat. Off. |
| 1082624 | 9/1967 | United Kingdom |
| 1240513 | 7/1971 | United Kingdom |
| 2084172 | 4/1982 | United Kingdom |

OTHER PUBLICATIONS

Osbond, "Essential Fatty Acids Part I", Journal of Chemical Society, 1961, Part III, pp. 2779–2787.
Horrobin, "Evening Primerose Oil", *The Health Quaterly*, Issue 31, vol. 6, No. 5, pp. 18–19, 70+71, 1981.
Horrobin, "How do Polyunsaturated Fatty Acids Lower Plasma Cholesterol Levels?", *Lipids*, vol. 18, No. 8, 1983.
Traitler et al. "Characterization of γ-Linolenic Acid in Ribes Seed", *Lipids*, vol. 19, No. 12, 1984.
Blaton, et al., "Effects of Dietary Alpha-And Gamma Linolenic Supplement on Serum Lidpids", Prostaglandin and Platelet Function in Mau, Chemical Chemisty, 32: 242 (1986).
Sugano, et al., "Hyprocholester Device Effect of Gamma-Linedevic Acid as Ering Pruense Oil W. Rats", Ann. Nutri Metab, 30:289–299 (1986).
Sugano, et al., "Effects of Mold Oil Containing Y. Linolenic Acid on the Blood Cholesterol and Eicosanid Levels in Rats", Agric Biol. Chemi., 50 (10), 2483–2491 (1986).
Boberg et al., Effect of Dietary Supplementation With N-6 and N-3 Long-Chain Polyunsaturated.
Fatty Acids On Serm Lypopreteins and Platelet Function in Hyperhiglycaridarniee Pateients, Acta. Ged. Scand., 220:153–160 (1986).
Huang, et al., "The Effects of Dietary Cholesterol on Blood and Liver Polyuasatuated Fatty Acids and on Plasma Cholesterol in Rats Fed Various Types of Fatty Acid Diet", Lipids, vol. 19, No. 9, (1984) pp. 664–672.

*Primary Examiner*—John W. Rollins
*Attorney, Agent, or Firm*—Vogt & O'Donnell

[57] ABSTRACT

Lipid of blackcurrant seed is employed for treating of lipoprotein disorders associated with cholesterol metabolism. Its administration to humans produces an increase of cholesterol of the high-density lipoproteins and a reduction of the cholesterol of the low-density lipoproteins.

5 Claims, No Drawings

TREATMENT OF LIPOPROTEIN DISORDERS ASSOCIATED WITH CHOLESTEROL METABOLISM

BACKGROUND OF THE INVENTION

This invention relates to the use of a lipid of the blackcurrant in the treatment of lipoprotein disorders associated with cholesterol metabolism.

Lipids circulate in the blood in the form of lipoproteins soluble in aqueous medium which consist of a lipidic nucleus of cholesterol esterified by fatty acids and triglycerides surrounded by a layer of proteins, phospholipids and free cholesterol. The arrangement of the various components characterizes the type of lipoprotein. Numerous epidemiological studies have demonstrated the preponderant role played by the lipoproteins in the development of atherosclerosis.

In simple terms, it is known that certain lipoproteins, known as low-density lipoproteins (LDL), represent a cardiovascular risk factor because there is a positive correlation between their presence at high levels in the bloodstream and atherosclerosis. By contrast, high-density lipoproteins (HDL) represent an anti-cardiovascular risk factor because there is a negative correlation between their levels and the disease. There is thus a "good cholesterol" transported by the HDL which drain the cholesterol from the arterial wall and return it to the liver where it is catabolized. By contrast, the LDL deposit the cholesterol on the arterial wall.

It is known that oils rich in polyunsaturated fatty acids have the effect of reducing the total plasmatic cholesterol level (TC). However, studies have shown that the fall in the TC is due either to a concomitant reduction in the cholesterol of the LDL (CLDL) and the cholesterol of the HDL (CHDL) or to a reduction in the CLDL with no modification of the CHDL. According to D.V. Horrobin, et al., in Lipids, Vol. 18, No. 8, pages 558–561, this last case would be that of evening primrose oil.

Summary of the Invention

We have surprisingly found that the administration of blackcurrant seed oil produced a a reduction in the CLDL while significantly increasing the CHDL.

Accordingly, the present invention relates to the use of a lipid of the blackcurrant for preparing a dietetic or pharmaceutical composition for the treatment of lipoprotein disorders associated with cholesterol metabolism.

Description of the Invention

In the context of the invention, lipoprotein disorders associated with cholesterol metabolism are understood to include;

essential hypercholesterolemia (type IIa) characterized by a normal triglyceride level (TG), an increase in the TC corresponding to an increase in the CLDL and to a reduction in, or normal level of, the CHDL, mixed hyperlipidemia (type IIb) characterized by an increase in, or normal level of, the TG, an increase in, or normal level of, the TC corresponding to an increase in the CLDL and to a reduction in the CHDL, dys-beta-lipoproteinemia (type III) characterized by an increase in the TG and in the TC, the latter being distinctly less frequent than the other two, the anomaly corresponding to a low level of HDL.

In the context of the invention, lipid of the blackcurrant is understood to be:

the oil of blackcurrant seeds (*Ribes nigrum*) obtained by extraction from blackcurrant residues and refining, for example as described in European patent 92 085 or European patent application 137 862, a mixture of fatty acids emanating from the hydrolysis or fractionation of blackcurrant seed oil and obtained, for example, in accordance with European patent application no. 178 442 or in accordance with European patent application no 271 747.

a pharmaceutcially acceptable salt of the fatty acids mentioned above, an oil obtained by re-esterification of such a mixture of fatty acids with glycerol, a mixture of the lipids mentioned above.

The blackcurrant lipid may advantageously be protected against oxidation by a liposoluble antioxidant, for example ascorbyl palmitate, tocopherols or a mixture of such antioxidants.

The dietetic compositions may be formulated as emulsions, for example sauces, mayonnaises or margarines.

The pharmaceutical compositions may be made up in various forms according to the method of administration, for example oral, enteral, rectal or parenteral. For example, it is possible to prepare capsules, gelatin-coated tablets, suppositories or syrups. In the case of enteral or parenteral administration, the compositions are formulated as physically and chemically stabilized, apyrogenic and sterile solutions or emulsions.

The dose administered depends upon the type and seriousness of the anomaly to be treated. It may comprise from 1 to 25 g blackcurrant lipid and preferably from 2 to 5 g blackcurrant oil daily in a single dose or preferably in two to three separate doses.

Example

The invention is illustrated by the following Example in which the parts and percentages are by weight, unless otherwise indicated.

EXPERIMENTAL CONDITIONS

Patients having an initial TC level of more than 300 mg/dl are treated for 12 weeks with an average daily dose of six gelatin capsules containing either 450 mg blackcurrant seed oil (BCO) and 200 ppm (parts per million) ascorbyl palmitate or 450 mg grapeseed oil (GSO) and 200 ppm ascorbyl palmitate.

BCO consists of triglycerides of the following fatty acids (by weight):

| | |
|---|---|
| linoleic acid, $C_{18:2,n-6}$ | 45% |
| gamma-linolenic acid, $C_{18:3,n-6}$ with 38% in the beta-position | 17% |
| alpha-linolenic acid, $C_{18:3,n-3}$ with 17% in the beta-position | 13% |
| stearidonic acid, $C_{18:4,n-3}$ with 32% in the beta-position | 3.5% |

Gamma-linolenic acid is the reaction product of delta-6-desaturase with linoleic acid.

Stearidonic acid is the reaction product of delta-6-desaturase with alpha-linolenic acid.

GSO contains approximately 70% by weight linoleic acid, 1 to 2% by weight alpha-linolenic acid, but no gammalinolenic acid or stearidonic acid.

All the patients were given an information sheet of dietetic recommendations.

The group receiving the BCO consisted of 5 patients comprising 3 females and 2 males with an average age of 61 years (from 36 to 76). The group receiving the GSO consisted of 7 patients, 4 females and 3 males, with an average age of 55 years (from 48 to 62). In the two groups, the initial TC was similar. In the two groups, the majority of patients were of the IIb type defined above.

Blood samples were taken at intervals of 0, 4, 8 and 12 weeks for analysis of the parameters.

Results

Table 1 below shows the mean values of the parameters indicated ($\bar{X}$) and the standard deviations (SD) for each visit and the probability of the statistical test (T test) for the two groups. The T test provides an answer to the question: is there any difference between the means of the groups studied and that for each visit? The significant cases (probability $\leq 0.05$) are underlined.

The TC (mg/dl) is measured enzymatically from the serum by colorimetry using the enzymes cholesterolesterase, cholesteroloxidase and the indicator 4-aminophenazine.

The CHDL (mg/dl) is measured in the same way as the TC on the fraction containing the HDL collected after ultracentrifugation of the serum at 12,000 r.p.m.

The CLDL (mg/dl) is deduced from the value of the CHDL in accordance with Friedewald and Fredrickson.

Table 2 relates to the probabilities of the paired T tests between the visits $V_4$, $V_8$, $V_{12}$ and $V_0$. The object of these statistical tests is to find the differences between the visit $V_o$ and the successive visits $V_4$, $V_8$ and $V_{12}$ for each group taken separately, i.e., the evolution of the phenomenon as a function of time. Once again the significant cases are underlined (probability $\leq 0.05$).

Table 3 below studies the $$\frac{CLDL}{CHDL}$$

ratio known as the "standard atherogenicity risk" and the probabilities of the T test. Table 4 below shows the probabilities of the paired T tests. The significant cases are underlined.

TABLE 2

| Parameters Between visits | | TC | | | CHDL | | | CLDL | | |
|---|---|---|---|---|---|---|---|---|---|---|
| | | $V_4 - V_0$ | $V_8 - V_0$ | $V_{12} - V_0$ | $V_4 - V_0$ | $V_8 - V_0$ | $V_{12} - V_0$ | $V_4 - V_0$ | $V_8 - V_0$ | $V_{12} - V_0$ |
| BCO Group Probability | n = 5 | <u>0.003</u> | <u>0.040</u> | <u>0.010</u> | 0.233 | <u>0.025</u> | <u>0.010</u> | 0.066 | <u>0.016</u> | 0.002 |
| GS0 GROUP Probability | n = 7 | <u>0.045</u> | 0.219 | 0.143 | <u>0.030</u> | 0.408 | 0.233 | 0.303 | <u>0.028</u> | 0.393 |

TABLE 3

| Groups | | n | CLDL/CHDL | | | |
|---|---|---|---|---|---|---|
| | | | 0 | 4 | 8 | 12 |
| BCO | $\bar{X}$ | 5 | 6.34 | 5.63 | 4.24 | 3.48 |
| | SD | 5 | 0.44 | 0.95 | 0.34 | 0.38 |
| GS0 | $\bar{X}$ | 7 | 6.86 | 6.97 | 6.35 | 6.93 |
| | SD | 7 | 0.45 | 0.42 | 0.49 | 0.56 |
| Probability | | | 0.445 | 0.184 | <u>0.010</u> | <u>0.010</u> |

TABLE 4

| Between visits | | $V_4 - V_0$ | $V_8 - V_0$ | $V_{12} - V_0$ |
|---|---|---|---|---|
| BCO group | n = 5 | 0.259 | <u>≤0.001</u> | <u>≤0.001</u> |
| GS0 group Probability | n = 7 | 0.298 | 0.0155 | 0.740 |

TABLE 1

| GROUPS | | n | CT | | | | CHDL | | | | CLDL | | | |
|---|---|---|---|---|---|---|---|---|---|---|---|---|---|---|
| | | | 0 | 4 | 8 | 12 | 0 | 4 | 8 | 12 | 0 | 4 | 8 | 12 |
| BCO | $\bar{X}$ | 5 | 309.20 | 293.40 | 279.20 | 261.00 | 42.80 | 50.20 | 56.40 | 61.40 | 270.20 | 260.00 | 234.20 | 206.60 |
| | SD | 5 | 4.49 | 3.94 | 6.27 | 9.57 | 1.91 | 2.04 | 1.92 | 1.43 | 13.73 | 12.30 | 14.21 | 17.82 |
| GS0 | $\bar{X}$ | 7 | 304.43 | 295.00 | 298.43 | 293.71 | 40.86 | 39.71 | 42.71 | 39.57 | 276.57 | 273.00 | 267.14 | 271.28 |
| | SD | 7 | 4.63 | 7.12 | 6.27 | 9.57 | 1.91 | 2.04 | 1.92 | 1.43 | 13.73 | 12.29 | 14.21 | 17.82 |
| Probability | | | 0.492 | 0.865 | 0.079 | <u>0.033</u> | 0.526 | 0.130 | <u>0.029</u> | <u>0.001</u> | 0.790 | 0.593 | 0.191 | <u>0.021</u> |

Conclusions

In the BCO group, the mean of the CHDL increased distinctly (+43.5%), the means of the CLDL and the TC decreased (−23.5% and −15.6%, respectively) and the mean of the standard atherogenicity risk factor decreased from 6.34 to 3.48 during the treatment.

By comparison, the corresponding values of the GSO group were: CHDL (−3.2%), CLDL (−1.9%), TC (−3.5%)

The mean of the standard atherogenicity risk factor showed hardly any change (from 6.86 to 6.93).

It can thus be seen that the administration of BCO leads to a reduction in the TC due solely to a decrease in the CLDL without participation of the CHDL which, by contrast, increases substantially. The standard atherogenicity risk thus decreases considerably.

By contrast, the administration of GSO produces no improvement in the pathological state of the patients.

We claim:

1. A method for treatment of lipoprotein disorders associated with cholesterol metabolism comprising administering blackcurrant lipid to humans having such disorders in an amount effective for, over time, increasing CHDL and reducing CLDL levels in the humans.

2. A method according to claim 1 wherein a daily dose of from 1 g to 25 g of blackcurrant lipid is administered.

3. A method according to claim 1 wherein a daily dose of from 2 g to 5 g of blackcurrant seed oil is administered.

4. A method according to claim 1 wherein the blackcurrant lipid is administered in a form of a pharmaceutical composition selected from the group of forms for administration consisting of forms for oral, enteral, rectal and parental administration.

5. A method according to claim 1 wherein the blackcurrant lipid is administered in a form of a dietetic composition.

* * * * *

UNITED STATES PATENT AND TRADEMARK OFFICE
CERTIFICATE OF CORRECTION

PATENT NO. : 4,999,380

DATED : March 12, 1991

INVENTOR(S) : Manfred BERGER, et al.

It is certified that error appears in the above-identified patent and that said Letters Patent is hereby corrected as shown below:

On the title page, under the heading "OTHER PUBLICATIONS", in the title of the first cited Horrobin reference, "Primerose" should be --Primrose--.

On the title page, under the heading "OTHER PUBLICATIONS", the title of the first cited Sugano, et al., reference should be --Hypocholesterolemic Effect of Gamma-Linolenic Acid as Evening Primrose Oil in Rats--.

On the title page, under the heading "OTHER PUBLICATIONS", in the title of the Boberg, et al. reference, "Hyperhiglycaridarniee Pateients" sjhould be --Hypertriglyceridaemic Patients-- and "Ged." should be --Med.--.

UNITED STATES PATENT AND TRADEMARK OFFICE
CERTIFICATE OF CORRECTION

PATENT NO. : 4,999,380

DATED : March 12, 1991

INVENTOR(S) : Manfred BERGER, et al.

It is certified that error appears in the above-identified patent and that said Letters Patent is hereby corrected as shown below:

On the title page under the heading "OTHER PUBLICATIONS" in the title of the Huang, et al., reference, "Polyuasatuated" should be --Polyunsaturated--.

In the ABSTRACT, line 1, "treating" should be --treatment--.

Signed and Sealed this

Twelfth Day of January, 1993

Attest:

DOUGLAS B. COMER

*Attesting Officer*     Acting Commissioner of Patents and Trademarks